US00PP32067P2

(12) United States Plant Patent
Hansen

(10) Patent No.: US PP32,067 P2
(45) Date of Patent: Aug. 11, 2020

(54) ***HOSTA* PLANT NAMED 'ROYAL CREST'**

(50) Latin Name: ***Hosta* hybrid (Tratt.)**
Varietal Denomination: Royal Crest

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/602,621

(22) Filed: Nov. 8, 2019

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
CPC ... A01H 5/12; A01H 5/02; A01H 5/00; A01H 6/12; A01H 6/56
See application file for complete search history.

*Primary Examiner* — June Hwu

(57) ABSTRACT

A new and distinct *Hosta* plant named 'Royal Crest' with medium rounded-mound habit of heavy-substance, cordate foliage having slightly wavy margins, acute apex and cordate base with deep green color. The plant has large, white, strongly-fragrant, broadly-faced flowers densely arranged on stiff upright scapes above the foliage beginning in early August.

2 Drawing Sheets

Latin name and variety denomination of the plant:
Botanical classification: *Hosta* hybrid (Tratt.).
Variety denomination: 'Royal Crest'.

STATEMENT REGARDING PRIOR DISCLOSURES UNDER 37 CFR 1.77(B)(6)

The first public disclosure of the claimed plant, in the form of a website to the public and email release to customers, was made by Walters Gardens, Inc. on Feb. 1, 2018 followed by the Walters Gardens, Inc. Summer 2018-Spring 2019 catalog on Jun. 5, 2018. The first public sales of *Hosta* 'Royal Crest' was by Walters Gardens, Inc. on Jun. 10, 2019. Walters Gardens, Inc. obtained the new plant and information about the new plant directly from the inventor. No plants of *Hosta* 'Royal Crest' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct *hosta* plant, *Hosta* 'Royal Crest' hereinafter also referred to as the new plant or just the cultivar name, 'Royal Crest'. *Hosta* 'Royal Crest' was a cross by the inventor at a wholesale nursery in Zeeland, Mich., USA on Aug. 31, 2009. The female parent was a proprietary, induced, tetraploid mutation of 'Royal Standard' (not patented). The male parent was 'Braveheart' (not patented). The new plant passed the initial evaluation in 2011 and was assigned the breeder code H9-109-01 through the remaining trial period. The new plant has been asexually propagated by division at the same nursery in Zeeland, Mich., USA since 2014 and also by careful plant shoot-tip tissue culture with the resultant asexually propagated plants having retained all the same traits as the original plant.

BRIEF SUMMARY OF THE PLANT

There are over 6,000 registered *hosta* cultivars with The American *Hosta* Society, which is the International Cultivar Registration Authority for the genus *Hosta* along with a similar number of unregistered cultivars. The nearest known comparison cultivars are *Hosta* 'Braveheart', 'Old Faithful' (not patented), 'Fried Green Tomatoes' (not patented) and 'Royal Standard' (not patented).

All of the above plants have fragrant flowers. 'Braveheart' has a smaller foliage, flatter habit and more lavender flowers. 'Old Faithful' has more lavender flower buds and very pale lavender flowers that are not as white, the scapes are more arching, the petioles tend to have a reddish coloring near the base, and it forms a larger clump. 'Fried Green Tomatoes' has solid green foliage, but the leaves are more arching and the leaf substance is not as thick, the flower stems are more outwardly and the tepals are a very pale lavender. 'Fried Green Tomatoes' flower about two weeks earlier than the new plant. 'Royal Standard' has solid green foliage, but the leaves are more arching and the leaf substance is not as thick.

Other *Hosta* cultivars have variegated foliage, but 'Royal Crest' is distinct from the above listed *hostas* and all other cultivars known to the inventor by the following combined traits:

1. Medium rounded-mound plant habit with dense foliage with deep green leaves;
2. Heavy-substance, stiff leaves of cordate shape and acute apex and cordate base;
3. Leaves moderately shiny surface above and strongly shiny below with slightly sinuate margins;
4. Large flowers on stiff upwardly projecting scapes above foliage are white, broad-faced, strongly-fragrant beginning in early August.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
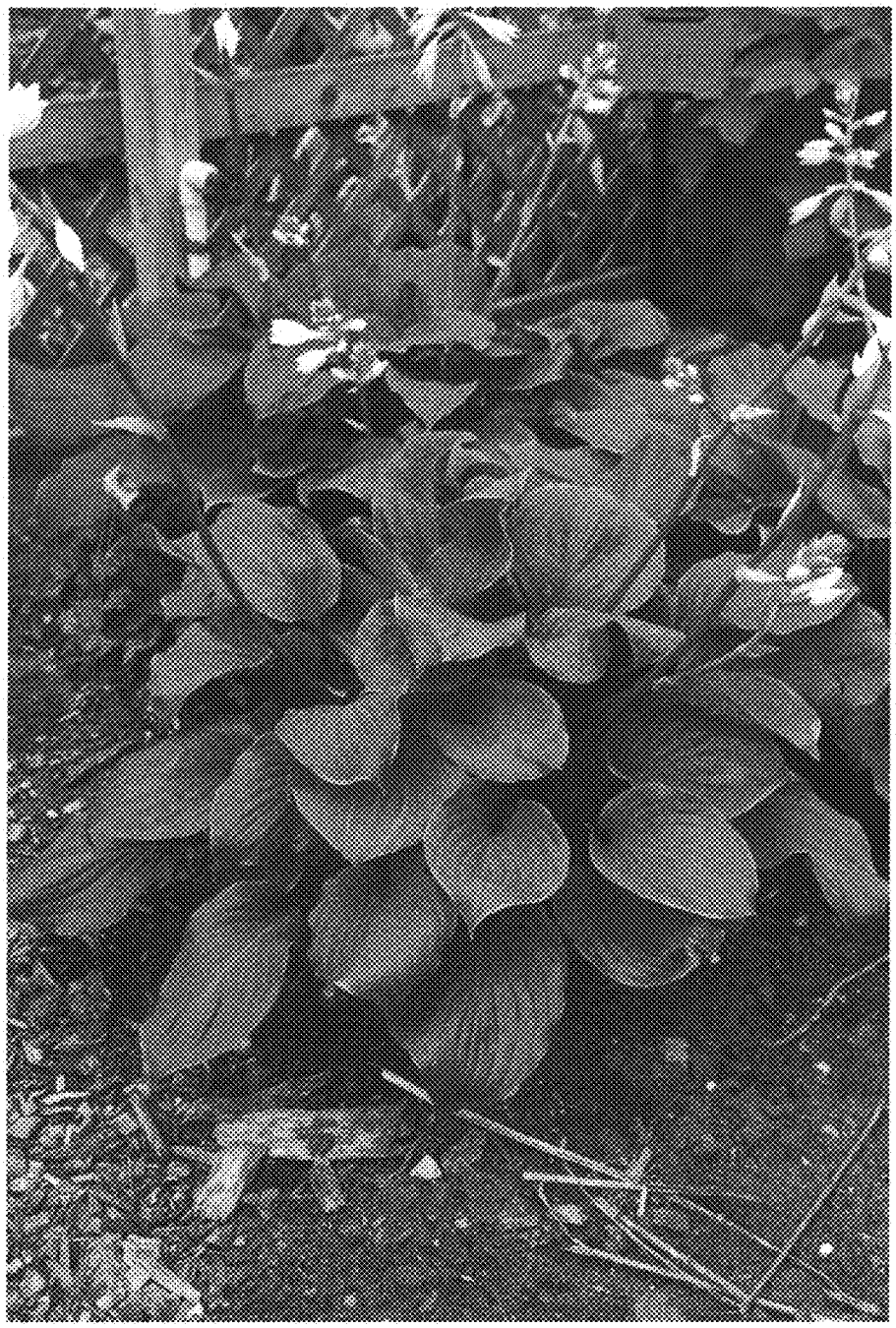
FIG. 1 shows a side view of a five-year-old plant showing the mounded plant habit.
Figure 2:
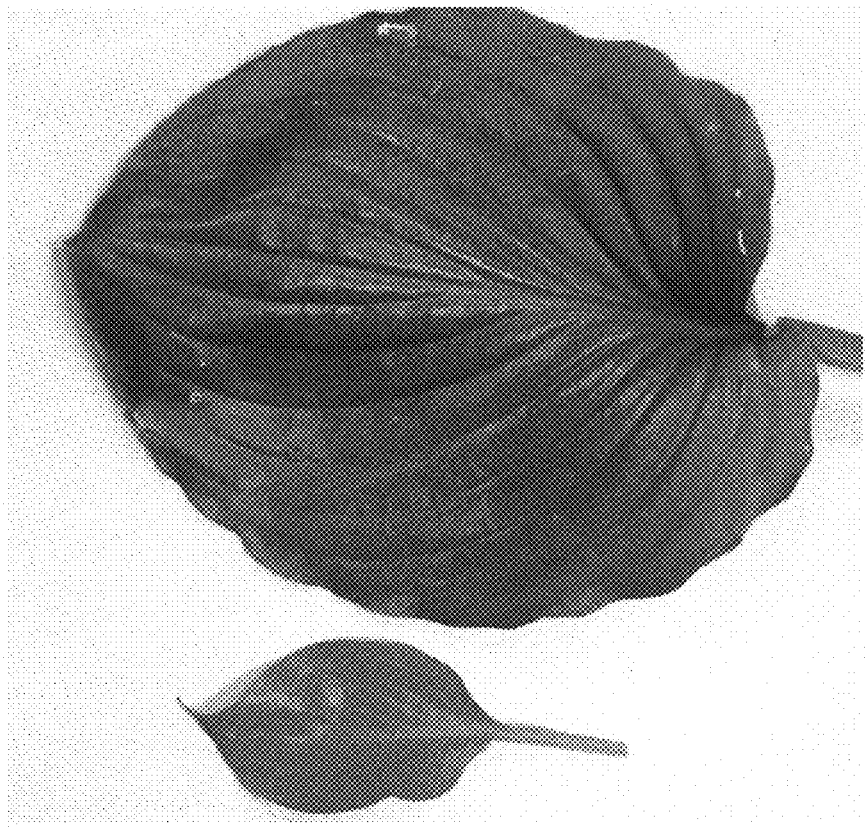
FIG. 2 shows a close-up of the foliage with top leaf mature and bottom leaf emerging.
Figure 3:
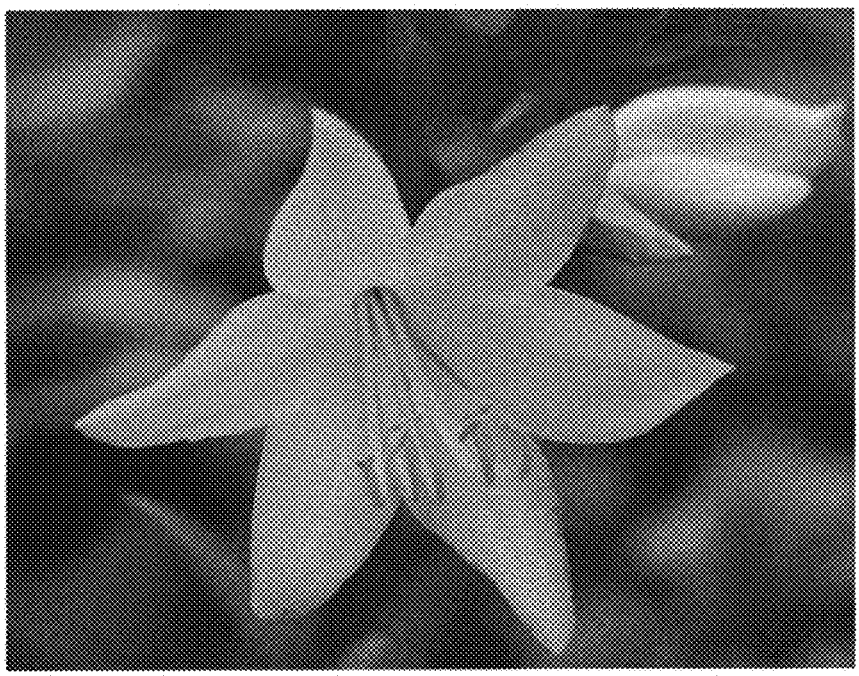
FIG. 3 shows a close-up of the flower and buds.

The following descriptions and color references are based on the 2015 edition of The Royal Horticultural Society Colour Chart except where common dictionary terms are used. The new plant, *Hosta* 'Royal Crest', has not been observed under all possible environments. The phenotype may vary slightly with different environmental conditions, such as temperature, light, fertility, moisture and maturity levels, but without any change in the genotype. The following observations and size descriptions are of a five-year old plant in a partially shaded trial garden and container grown plant in a greenhouse in Zeeland, Mich. with supplemental water and fertilizer.

Botanical classification: *Hosta* hybrid;

Parentage: The female or seed parent is a select, proprietary induced tetraploid plant from 'Royal Standard'; the male or pollen parent is 'Braveheart';

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching; color between RHS NN155B and RHS NN155C;

Plant shape and habit: Hardy herbaceous perennial with basal rosettes of leaves emerging from rhizomes producing a short, symmetrical, rounded-mound of leaves; about 14 divisions per plant; divisions to about 3.8 cm diameter at soil level;

Plant size: Foliage height to about 58.0 cm above soil line to the top of the leaves and about 125.0 cm wide at the widest point about 35 cm above the soil line;

Foliage description: Glabrous, moderately lustrous adaxial and very lustrous abaxial; cordate, with acute apex and cordate base; entire margin, slightly sinuate; blades mostly flat, without folding or twisting; with a thicker stiffer feel than 'Royal Standard';

Leaf blade size: To about 28.5 cm long, 20.5 cm wide near middle;

Leaf blade color: Early season and expanding adaxial center and margin nearest RHS 138B and abaxial nearest RHS 146B; mid-season and later adaxial center and margin nearest blend of RHS NN137A and RHS 139A;

Petiole: Entire, glabrous, glabrous, concavo-convex; mostly straight from base of plant to leaf base with little to no bending or curving, only slightly flexible; outwardly; to about 44.0 cm long, 32.0 cm wide at base and 18 mm deep at base and 10 mm deep below blade;

Petiole color: Adaxial center nearest RHS 146D and along margin nearest RHS 146B; abaxial center nearest RHS 145C and along margin nearest RHS 137B;

Veins: Parallel, lightly impressed adaxial, moderately costate on abaxial side; about 10 to 12 pairs and one main center vein;

Veins color: Adaxial midrib and secondary veins nearest blend of RHS NN137A and RHS 139A; abaxial midrib basal one-half nearest RHS 145D, distal one-half and secondary veins nearest RHS 146C;

Flower description: Perfect; single; actinomorphic; funnel-form, with distally flaring tepals forming nearly flat face; held outwardly; persist for normal period, usually one day on plant or as cut flower;

Flower period: Scapes remain effective with flowering beginning early August for about four to five weeks in Michigan;

Size: About 80.0 mm long with exserted style and stamens; corolla to about 62.0 mm long and flared to about 75.0 mm across; corolla tube to about 22.0 mm long and 7.0 mm diameter toward base;

Fragrance: Strongly sweet;

Tepals: Two sets of three; fused joints vitreous in distal 18.0 mm;

Inner tepal: Lanceolate, acute apex, fused in basal 42.0 mm, entire margin; 80.0 mm long and 18.0 mm across slightly above fusion; not vitreous along margin;

Inner tepal color: Adaxial and abaxial nearest RHS NN155D; abaxial basal 2.0 mm nearest RHS NN155B, apical 0.5 mm frequently tipped nearest RHS 143A;

Outer tepal: Lanceolate, acute apex, fused in basal 42.0 mm, entire margin; 80.0 mm long and 20.0 mm across slightly above fusion; not vitreous along margin;

Outer tepal color: Adaxial and abaxial nearest RHS NN155D; abaxial basal 2.0 mm nearest RHS NN155B, apical 0.5 mm frequently tipped nearest RHS 143A;

Gynoecium: Single; tri-carpelled; superior; 84.0 mm long;

*Style*.—Single; cylindrical; arcuate 90 degrees upward in distal 10.0 mm; basal 7.0 mm adnate to inner corolla; color nearest RHS NN155B in distal 15.0 mm and proximally nearest RHS NN155D.

*Stigma*.—Globose, micro-puberulent; about 2.0 mm across and 2.0 mm tall; tri-lobed; color nearest RHS 13D.

*Ovary*.—Ellipsoidal; longitudinally fluted; acute apex, truncate base; about 10.0 mm long and 3.5 mm diameter; color nearest RHS 145C.

Androecium:

*Filaments*.—Typically six; cylindrical; glabrous; arcuate upward in distal 10.0 mm; about 72.0 mm long and 1.5 mm diameter; color nearest RHS NN155D.

*Anthers*.—Oblong: dorsifixed, longitudinally dehiscent; fluted longitudinally; about 6.0 mm long and 2.5 mm across and 1.5 mm thick; color dorsal nearest RHS 11D, ventral nearest RHS 10A.

*Pollen*.—Smaller than 0.1 mm diameter; color nearest RHS 13A.

Flower bud: Clavate; with acute apex and fused tubular base, rounded proximally; about 57.0 mm long in total and 18.0 mm wide in bulb portion, tube about 20.0 mm long and 7.0 mm diameter;

Flower bud color: Tube nearest RHS NN155D; with apical bulb nearest RHS 143A;

Floral bracts: Subtending individual flowers; lanceolate to linear, narrowly acute apex, truncate clasping base, margin entire; moderately lustrous adaxial and abaxial; to about 30.0 mm long and 15.0 mm across, decreasing in size distally;

Bract color: Adaxial nearest RHS 138B and abaxial nearest RHS 138B;

Cauline bracts: Typically three below flowers; lanceolate; narrowly acute apex; truncate clasping base; moderately lustrous adaxial and abaxial; about 4.5 cm long and 10.0 mm diameter; color adaxial and abaxial nearest RHS 138B, dehiscing as flowers open;

Pedicel: Cylindrical, glabrous, lustrous; curved outwardly; to about 8.0 mm long and 4.0 mm diameter;

Pedicel color: Nearest RHS NN155C;

Peduncle: Cylindrical; usually one per mature division and eleven per plant; slightly glaucous, glabrous; erect; very stiff; length about 98.0 cm long and about 13.0 mm diameter;

Peduncle color: When flowering nearest RHS 137B;

Fruit: Cylindrical; apex frequently apiculate; base rounded; tri-valved, longitudinally dehiscent capsule; about 37.0 mm long and 9.0 mm diameter; color at maturity nearest RHS 161D with RHS 199D;

Seeds: Up to about 33 per capsule; endospermic; flattened-elliptic wing surrounding embryo situated toward one end of ellipse; up to about 10.0 mm long and 4.0 mm wide and 1.5 mm thick at embryo; color nearest RHS 202A;

Disease tolerance and resistance: The new plant has shown slight resistance to general slug feeding compared with other fragrant-flowered *hostas*. Other resistance has not been noted. The plant grows best and shows best coloration with plenty of moisture, adequate drainage and light shade, but is able to tolerate some drought when mature. Hardiness at least from USDA zone 3 through 9, and other disease resistance is typical of that of other *hostas*.

It is claimed:

1. A new and distinct ornamental plant cultivar named *Hosta* 'Royal Crest' as herein described and illustrated.

* * * * *